(12) United States Patent
Broman

(10) Patent No.: US 6,450,131 B1
(45) Date of Patent: Sep. 17, 2002

(54) FORWARD BENDING MOTION CONTROL HARNESS

(76) Inventor: Daniel James Broman, 172 Wren Dr., Duluth, MN (US) 55811

( * ) Notice: Subject to any disclaimer, the term of this patent is extended or adjusted under 35 U.S.C. 154(b) by 0 days.

(21) Appl. No.: 09/883,791

(22) Filed: Jun. 18, 2001

(51) Int. Cl.[7] .............................................. A62B 35/00
(52) U.S. Cl. ....................................... 119/857; 602/19
(58) Field of Search ................................. 119/857, 770, 119/769; 482/69, 70, 140, 141, 124; 182/3, 4, 6; 602/19

(56) References Cited

U.S. PATENT DOCUMENTS

| | | | | |
|---|---|---|---|---|
| 554,636 A | * | 2/1896 | Hulsmann | 482/124 |
| 634,404 A | * | 10/1899 | Asche | 254/45 |
| 1,409,326 A | * | 3/1922 | Williamson | 2/44 |
| 1,618,273 A | * | 2/1927 | Davidson | 482/124 |
| 2,699,284 A | * | 1/1955 | Rose | 119/857 |
| 3,424,134 A | * | 1/1969 | Rosenblum | 182/3 |
| 5,122,107 A | * | 6/1992 | Gardner | 482/140 |
| 5,203,829 A | * | 4/1993 | Fisk et al. | 119/857 |
| 5,372,565 A | * | 12/1994 | Burdenko | 482/124 |
| 5,643,184 A | * | 7/1997 | Toso | 2/44 |
| 5,716,307 A | * | 2/1998 | Vadher | 482/124 |
| 5,860,944 A | * | 1/1999 | Hoffman, Jr. | 2/44 |
| 5,957,091 A | * | 9/1999 | McDonald et al. | 119/770 |
| 6,129,691 A | * | 10/2000 | Ruppert | 128/845 |
| 6,367,582 B1 | * | 4/2002 | Derby | 119/857 |

FOREIGN PATENT DOCUMENTS

FR  2551628  * 9/1983

* cited by examiner

*Primary Examiner*—Yvonne R. Abbott
(74) *Attorney, Agent, or Firm*—Nikolai & Mersereau, P.A.

(57) ABSTRACT

A harness for preventing lower back injuries caused by improper bending and lifting. This harness consists of a flexible back strap (26), and two flexible shoulder straps. Two additional straps compose the lower portion of this device. The lower left strap (56) has one end connected to the left foot, while the lower right strap (38) has one end connected to the right foot. The other two ends of these straps are connected to each other using a strap-locking buckle (52). This buckle can be used to easily adjust the combined length of these two straps. Once properly adjusted, this harness prevents the wearer from forward bending past a pre-determined angle, which can be modified using the strap-locking buckle (52). As the wearer bends properly by bending their knees, this maximum forward bending angle increases just enough to allow the wearer to squat bend unrestricted.

12 Claims, 4 Drawing Sheets

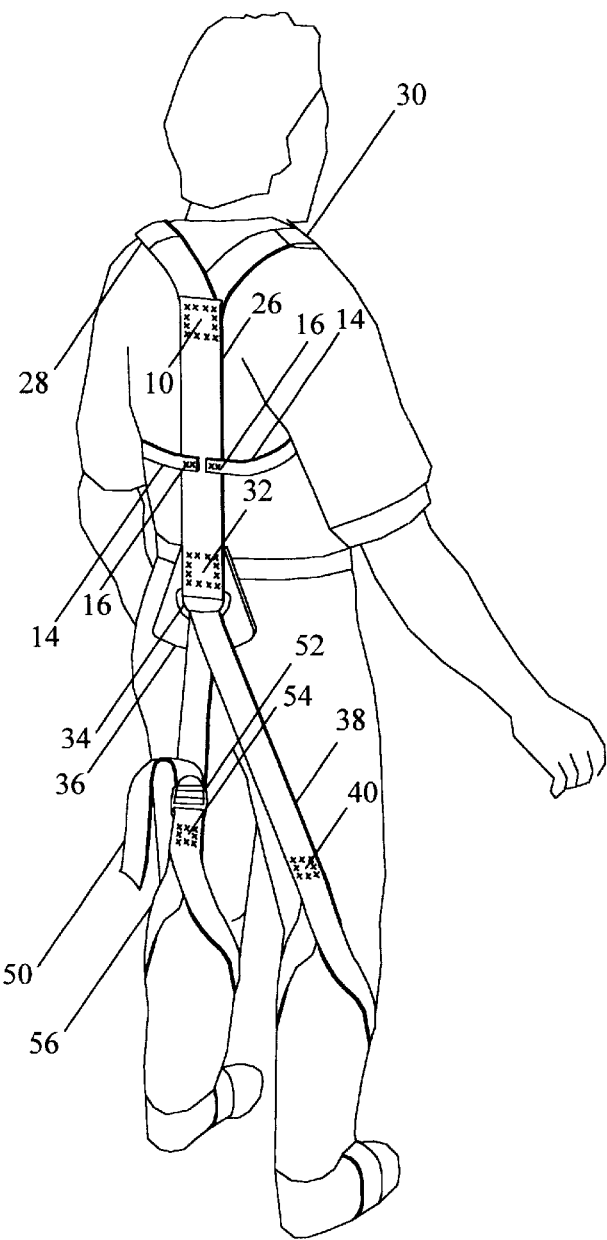 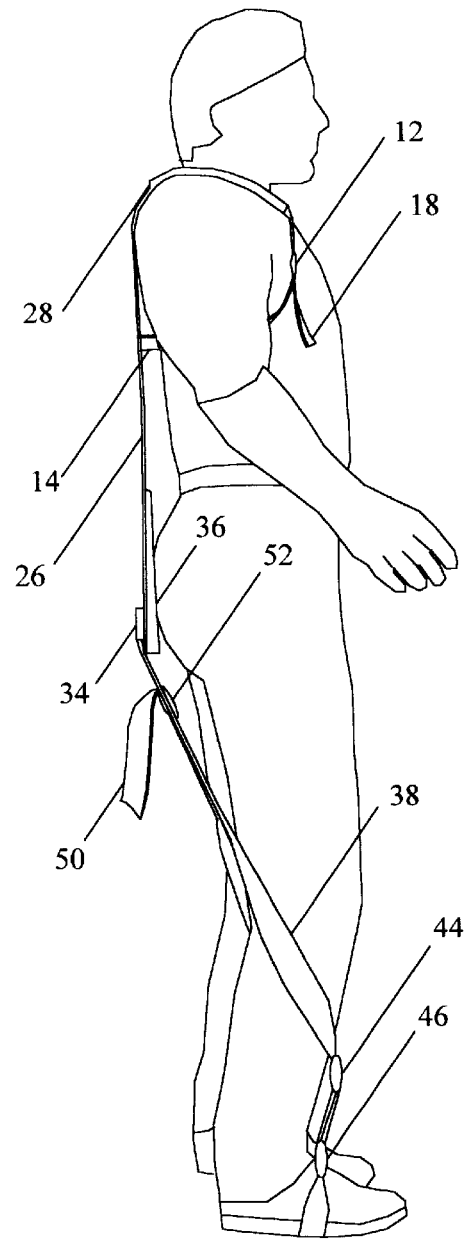
FIG.2
FIG.3

FORWARD BENDING MOTION CONTROL HARNESS

BACKGROUND OF THE INVENTION

1. Field of Invention

This invention relates generally to personal protective equipment worn to prevent injuries, more specifically, to safety devices worn to help prevent lower back injuries that can be caused by lifting and bending activities.

2. Description of the Related Art

Lower back injuries remain the most prevalent and costly work-related musculoskeletal disorder facing industry today, both in the United States and in other Western industrialized countries. According to the National Institute for Occupational Safety and Health (NIOSH), back injuries account for nearly 20% of all workplace injuries at a cost of between 20 and 50 billion dollars annually.

Forward bending is perhaps the most significant risk factor for back injury. When individuals bend over using the lower back as a fulcrum to manually lift or lower objects (forward bending), the upper body is supported by the lower back. As the upper body moves from an upright position towards a bent position (approximately 90 degrees), the forces required by the lower back muscles to support the upper body increase dramatically due to the increased moment arm. During forward bending, the ligaments along the back portion of the spine are in an end-range stretch. They are stretched to their limit, making them vulnerable to being torn, especially if lifting something heavy. Perhaps most significantly during forward bending, the muscles in the lower back are fully stretched. When bending forward more than half way, the deep protective muscles of the lower back actually stop working! There is very little muscle protection to the lower back tissues in a position of full forward bending. All these loads are being placed on the discs, ligaments, and joints with very little muscle protection, and all of these stresses are magnified by the amount of time spent in forward bending.

There has been very little success in the search for ways to reduce the occurrence of back injuries related to lifting and bending, however, experts in this field still tend to agree that bending and lifting with proper technique (i.e. squat lifting with a straight back and bent knees) can help reduce the occurrence of lower back injuries. When you bend at the knees while you lift, you keep your back in alignment and let the stronger muscles in your thighs do the actual lifting. Many organizations have, or are developing programs, to protect against back injuries and teach proper lifting methods to their employees. Unfortunately, studies indicate that company educational programs do little to reduce the incidence of back pain. One reason there has been a lack of worker compliance with proper lifting technique, or squat lifting, may be because bending the knees lowers the torso which requires more energy than forward bending. Even workers who have been educated on proper lifting techniques may opt to bend or lift with improper form when fatigued.

Back belts are a type of safety device that have been very popular and are widely used. These belts typically wrap circumferentially around the lumbar region of the body, and are tightened to provide support to the lower back and abdomen. Many studies have been done in an attempt to determine if back belts help prevent injury, and despite their popularity, the scientific evidence tends to be against their use. No evidence currently exists which would indicate that back belts prevent injury, in fact, in one study those who wore back belts reported more back pain than workers who didn't wear them. Workers wearing back belts may experience a false sense of security, causing them to lift unsafe loads. It has also been theorized that the prolonged use of back belts can weaken the muscles of the lower back, leading to a higher risk of injury when they are not worn. Additionally, back belts do not prevent forward bending, which again may be the most significant risk factor for lower back injury. NIOSH has determined not to recommend the use of back belts to prevent injury, and does not consider back belts to be personal protective equipment. Several US patents exist on various back belts including U.S. Pat. No. 4,709,692 to Kirschenberg (1987), U.S. Pat. No. 4,348,774 to Woodson (1982), and U.S. Pat. No. 3,603,316 to Lehman (1971). Despite all of the evidence suggesting that they do not prevent back injury, many companies still require their employees to wear back belts.

Another group of back safety devices provide an external force to assist the lower back muscles when lifting or bending. These devices can vary greatly in design and appearance, but typically employ a spring or elastic material to provide this force. Several of these devices are described in U.S. Pat. No. 6,129,691 to Ruppert (2000), U.S. Pat. No. 5,860,944 to Hoffman (1999), U.S. Pat. No. 5,951,591 to Roberts (1999), U.S. Pat. No. 5,816,251 to Glisan (1998), U.S. Pat. No. 4,829,989 to Deamer (1989), U.S. Pat. No. 3,570,011 to Naig (1971), U.S. Pat. No. 2,906,260 to Myers (1959), U.S. Pat. No. 1,812,529 to Haulbrook (1931), U.S. Pat. No. 1,746,067 to Zwalley (1930), U.S. Pat. No. 1,641,027 to Feaster (1927), U.S. Pat. No. 1,634,621 to Martinez (1927), U.S. Pat. No. 1,544,162 to Vigne (1925), U.S. Pat. No. 1,553,874 to Nivens (1925), U.S. Pat. No. 1,371,690 to Kelly (1921), U.S. Pat. No. 1,384,299 to Brown (1921), U.S. Pat. No. 1,202,851 to Kelly (1916), U.S. Pat. No. 903,403 to Quick (1908), U.S. Pat. No. 836,802 to Daniel (1906), U.S. Pat. No. 703,477 to Russell (1902), U.S. Pat. No. 654,173 to Mendenhall (1900), U.S. Pat. No. 637,156 to Potts (1899) and U.S. Pat. No. 443,113 to Ray (1890). Although these devices take some of the load off of the lower back muscles, they do not prevent the forward bending motion, and accordingly, have not provided a satisfactory solution to lower back injuries caused by bending and lifting activities.

A variety of other unique back safety devices have been developed over the years, and are often referred to simply as back braces. These devices often include features similar to the back belts described above, but have additional straps usually attached to the thighs or shoulders, and often have rigid components that restrict certain motion. Some of these devices are described in U.S. Pat. No. 5,172,703 to Tiede (1992), U.S. Pat. No. 5,040,524 to Votel (1991), U.S. Pat. No. 3,521,623 to Nichols (1970), U.S. Pat. No. 3,029,810 to Martin (1962), U.S. Pat. No. 1,316,915 to Meyer (1919), U.S. Pat. No. 1,098,492 to Gibson (1914), U.S. Pat. No. 781,544 to McMurtry (1905), and U.S. Pat. No. 401,223 to Smith (1889). Some of these devices do somewhat restrict forward bending, such as U.S. Pat. No. 1,008,500 to Thornton (1911) and U.S. Pat. No. 1,191,769 to Curts (1916), however, as the forward bending motion is restricted with these devices, the ability of the wearer to bend properly using the squat bending method is also completely restricted. A recent U.S. Pat. No. 5,259,833 to Barnett (1993), describes a back brace designed to prevent forward bending. The back bending motion limiting apparatus described in this patent consists of a pair of shoulder straps connected to the wearer's pants. When these straps are tightened, they prevent the forward bending motion. Although this device can prevent forward bending, it also prevents the wearer from squat bending. None of the prior art described above can both prevent forward bending, and at the same time allow squat bending.

SUMMARY OF THE INVENTION

The invention uses a back strap connected to a pair of shoulder straps which limit the forward bending movement of a user in combination with leg straps attached to the back strap through a ring at the base of the back strap and the user's feet. The length of the combined leg straps, back strap and shoulder straps is adjustable to limit the degree of bending of the wearer while standing erect to a small angle of forward bending and limit the forward bending to a larger degree while squatting since there will be some slack created in the length of the combined restraint when in the squatting position. The length of the belt thereby prevents back injuries by limiting the forward bending of the wearer while standing erect, which is an improper position for heavy lifting by bending the back, while allowing bending of the back while in a squatting position for lifting objects while using the leg muscles which is the proper way to lift heavy objects, thus preventing injuries to the wearer.

OBJECTS OF THE INVENTION

Accordingly, several objects and advantages of the present invention are:

(a) To provide a back safety harness which will prevent the wearer from forward bending past a predetermined angle without restricting the wearer from squat bending (i.e. straight back, bent knees).

(b) To provide a back safety harness which, while preventing forward bending, does not restrict the wearer's ability to walk naturally or perform other normal activities such as sitting or climbing/descending stairs.

(c) To provide a back safety harness, which while preventing forward bending, does not interfere or restrict activities performed by the wearers shoulders, arms, and hands.

Furthermore, this safety harness is easy and convenient to use, small, light-weight, comfortable, durable, and can be easily and quickly adjusted to fit most any body type. Additionally, this device is made from very low cost, common components. Still further objects and advantages will become apparent from a consideration of the ensuing description and drawings.

BRIEF DESCRIPTION OF THE DRAWINGS

FIG. 2 shows a rear perspective view of a man wearing the forward bending motion control harness of FIG. 1.

FIG. 3 shows a side view of a man wearing the forward bending motion control harness of FIG. 1.

DESCRIPTION OF THE PREFERRED EMBODIMENTS

Figure 1:
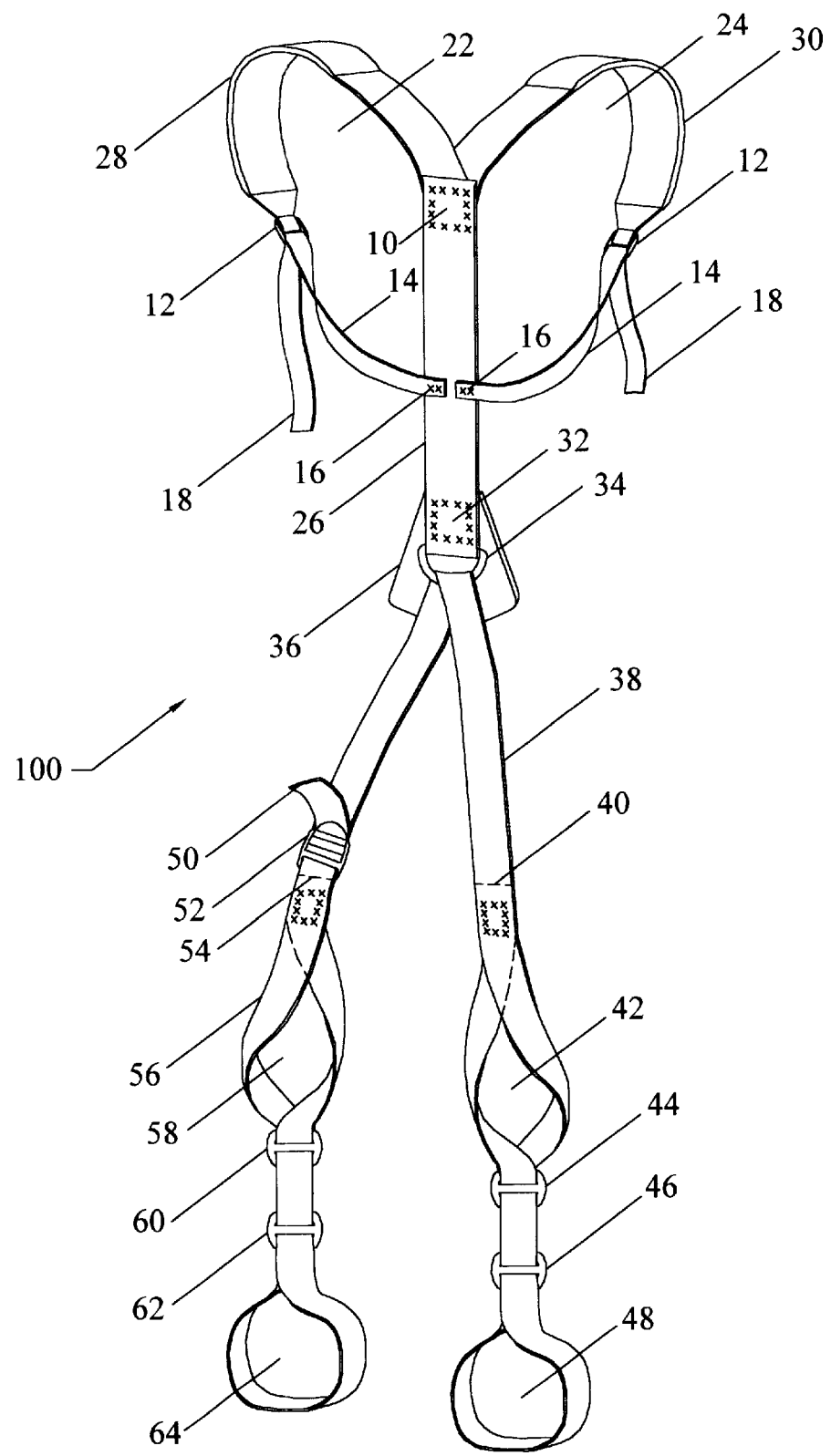
FIG. 1 shows a rear perspective view of one embodiment of a forward bending motion control harness.
Figure 6:
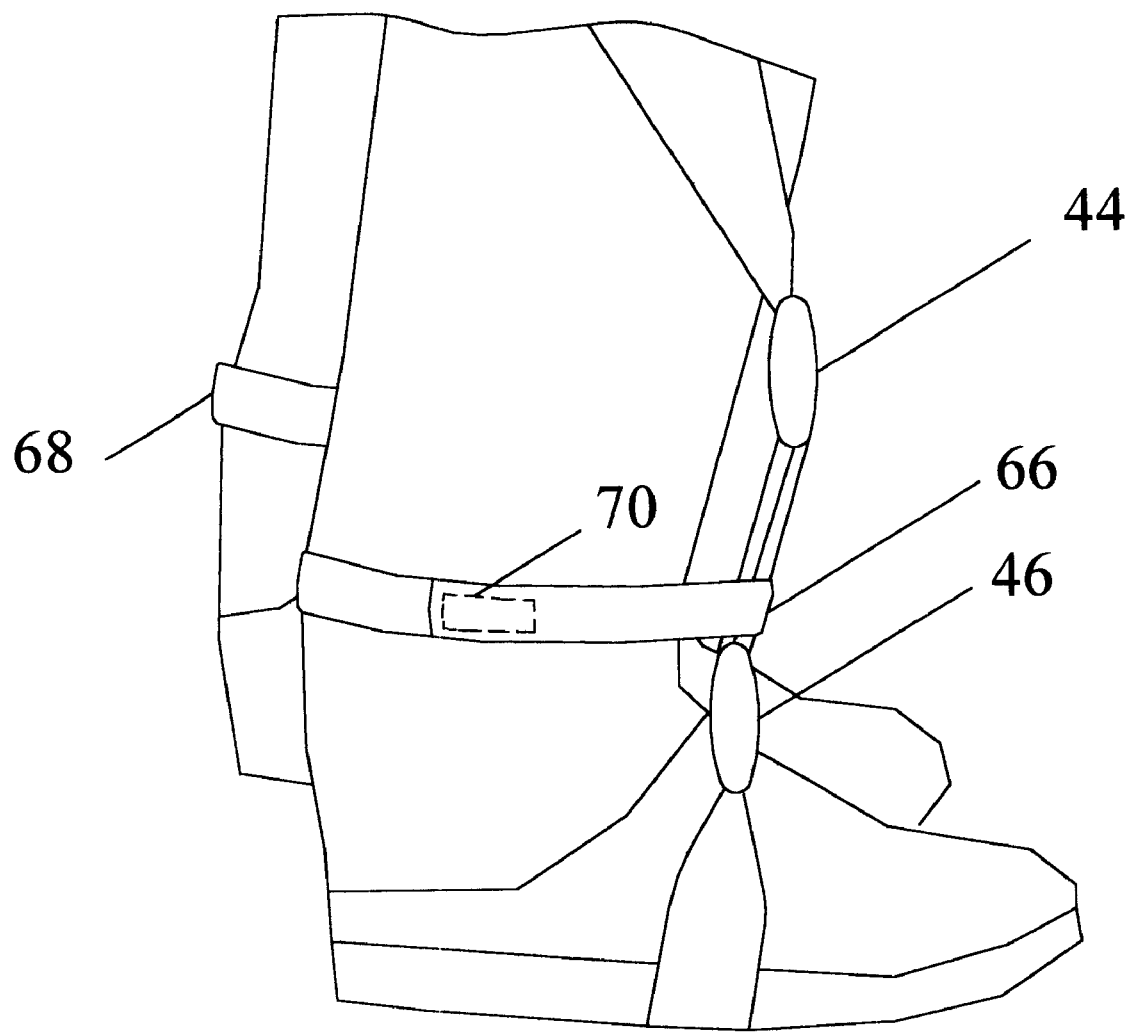
FIG. 6 is a cross sectional view of the lower legs and feet as seen in FIG. 3.

A typical embodiment of the forward bending motion control harness 100 is illustrated in FIG. 1. This harness has a flexible, centrally located back strap 26, which is approximately 0.6 meters (2 ft) long. A pair of flexible shoulder straps 28 and 30 are attached to the upper portion of the back strap 10 such as by stitching. Shoulder straps 28 and 30 each have a strap-locking buckle 12 connected to their respective ends. A strap-locking buckle is a commonly used buckle sometimes referred to as a ladder lock buckle or self-locking buckle. These buckles allow a strap to be easily pulled through them in one direction, and once the strap is pulled through it cannot slip back through the buckle in the opposite direction. Two connector straps 14 each have an end 16 attached to back strap 26. The fixed ends of these connector straps 16 should be connected low enough on back strap 26 such that they do not interfere with the free movement of the wearer's arms and shoulders. The free ends 18 of the connector straps 14 are threaded into each strap-locking buckle 12, creating left arm hole 22 and right arm hole 24. The lower end 32 of the back strap 26 is looped through D-ring 34 and sewn in place, securing D-ring 34 at the lower end of back strap 26. Pad 36 is positioned behind D-ring 34 and attached to the lower end 32 of the back strap 26. Lower left strap 56 has one end permanently secured to lower strap-locking buckle 52. Lower left strap 56 proceeds down through upper left slide adjuster 60 and lower left slide adjuster 62, wraps around to form left foot hole 64, and continues back up through slide adjusters 62 and 60. Finally, the end of this lower left strap 54 is sewn (or fastened in some other secure manner) onto lower left strap 56, creating left leg hole 58. Buckle 52 should be located no more than 7 or 8 cm (3 in.) from the point where end 54 is attached. For optimal performance, the total length of lower left strap 56 below the point where the end 54 is attached should be somewhere around 1.2 meters (4 feet). Lower right strap 38 is similar to lower left strap 56, however, lower right strap 38 has a free end 50 and is substantially longer to provide slack for any adjustments made using buckle 52. The free end of the lower right strap 50 is threaded through buckle 52. Lower right strap 38 then passes through D-ring 34 and proceeds through the upper and lower right slide adjusters 44 and 46. Lower right strap 38 then wraps around to form right foot hole 48, and winds back up through the slide adjusters 44 and 46 where end 40 is sewn (or fastened in some other secure manner) to lower right strap 38 creating right leg hole 42. The total length of lower right strap 38 below the point where end 40 is fastened should be approximately 1.2 meters (4 feet). The length of lower right strap 38 above the point where end 40 is attached should be approximately 1 meter (3.28 ft.). Nylon straps (and other similar straps) are available in several standard widths, but preferably, straps 56 and 38 should be composed of strap between 2.54 cm (1 inch) and 5.08 cm (2 inches) wide. All straps in the above description (14, 26, 28, 30, 38, 56) can be made from a variety of materials, but preferably should be made from non-stretch nylon webbing. Pad 36 could be made from a variety of materials as well, but heavy polyurethane foam enclosed in a durable fabric is preferable. Buckles 12 and 52, slide adjusters 44, 46, 60 and 62, and D-ring 34 described above are all widely available from retail fabric stores, and typically are composed of plastic or metal. Metal components could be used, but plastic components would be preferable because they are lighter, and will have sufficient strength to withstand normal forces generated while wearing this harness. Shoulder straps 28 and 30 should preferably be padded for additional comfort. Lower right strap 38 and lower left strap 56 were defined above as being on the right or left side as a way to clearly describe this device, however, in reality these straps could be worn on either leg. Two optional components of this device are shown in FIG. 6. The optional right leg strap 66 can be positioned in between the upper and lower right slide adjusters 44 and 46 as illustrated in FIG. 6. Optional left leg strap 68 is identical to optional right leg strap 66, and can be similarly positioned between upper and lower left slide adjusters 60 and 62. A hook and loop fastener 70 is illustrated in FIG. 6 as one method of securing the ends of these straps, however, nearly any type of buckle or fastener could be used.

Figures 4, 5:
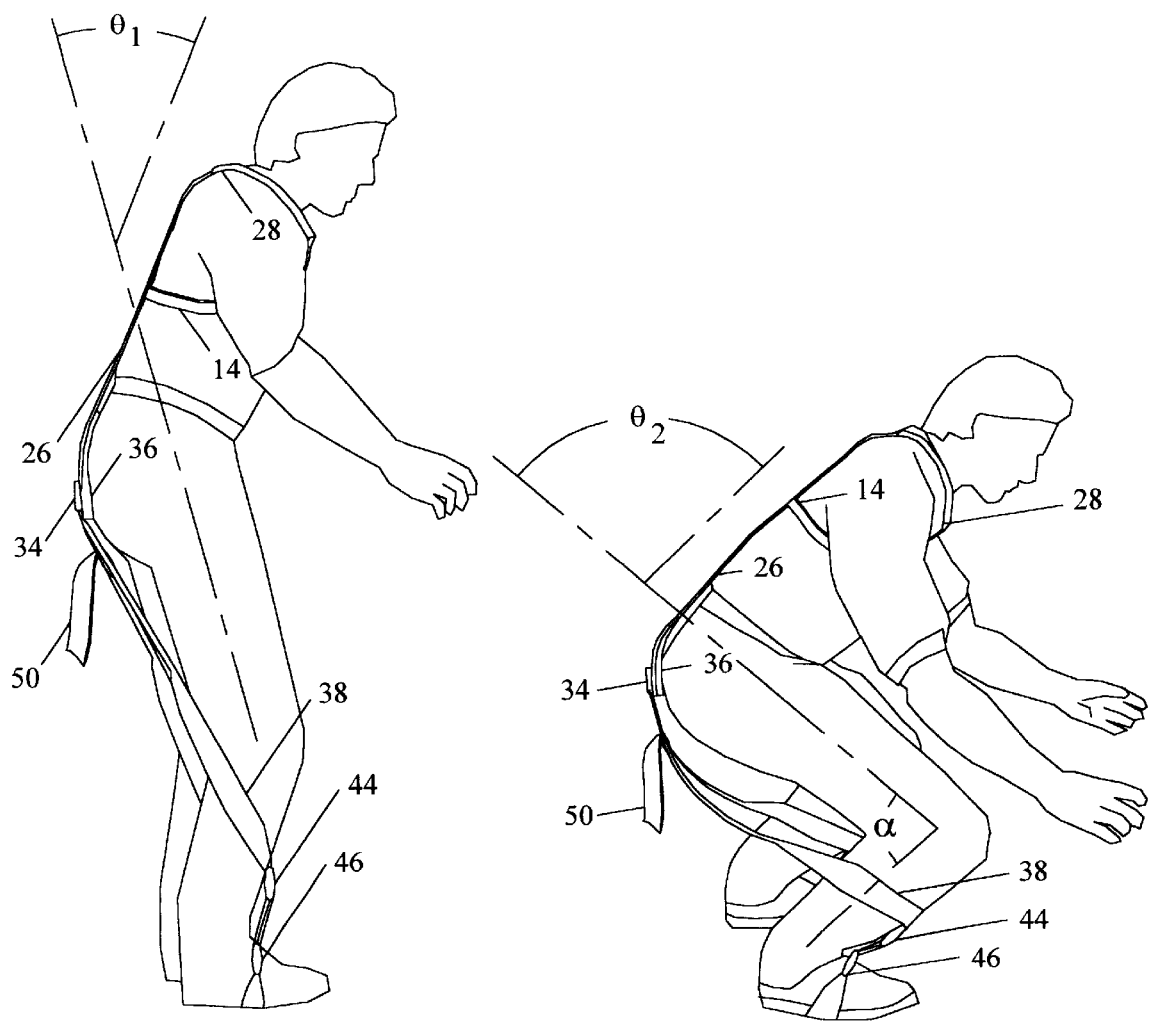
FIG. 4 is a side view of a man wearing this harness, which prevents the forward bending motion from exceeding the pre-adjusted angle θ.
FIG. 5 is a side view of a man wearing this harness, which illustrates the unrestricted motion of squat bending.

In order to use the harness 100, the wearer begins by positioning the harness 100 properly on their body and making the proper adjustments, as outlined below. Before attempting to use this harness 100, the wearer should first release additional slack in lower right strap 38 from buckle 52. This will make the process of putting on the harness 100 much easier, and allow the wearer to position the harness 100 properly on their body with greater ease. The wearer begins by placing their left arm through left arm hole 22 and their right arm through right arm hole 24 such that back strap 26 is centrally positioned along the wearer's back. FIG. 2 and FIG. 3 illustrate the correct positioning of the back strap 26 and shoulder straps 28 and 30. The wearer will then pull on the free ends of the connector straps 18 to tighten shoulder straps 28 and 30 around their shoulders and to position D-ring 34 such that it is centrally located on the wearers back, and such that it is located slightly below the wearer's waistline, as illustrated in FIG. 2. For optimal performance, D-ring 34 should be positioned about 13 cm below the waistline (approximately 5 inches). The wearer will then place their left leg through left leg hole 58, and their left foot into left foot hole 64, as illustrated in FIG. 2 and FIG. 3. Lower left slide adjuster 62 can then be lowered to tighten left foot hole 64 around the wearer's foot. The wearer will then place their right leg through right leg hole 42, and place their right foot into right foot hole 48 as illustrated in FIG. 2 and FIG. 3. Again, the wearer can now adjust slide adjuster 46 to tighten right foot hole 48 around the wearer's right foot. At this point, the wearer will pull on the free end of the lower right strap 50 which is threaded through buckle 52 in order to tighten the harness to achieve the desired maximum allowable forward bending angle θ illustrated in FIG. 4 and FIG. 5. Angle θ can be defined as the angle between a line parallel to the wearer's thigh and a line parallel to the wearer's back as illustrated in FIG. 4 and FIG. 5. $\theta_1$ shown in FIG. 4 represents the maximum allowable forward bending angle θ while the wearer is in the standing position. In FIG. 5, $\theta_2$ represents the maximum allowable forward bending angle θ while the wearer is in the squatting position. The more that lower right strap 38 is pulled through buckle 52, the smaller angle θ becomes. If θ becomes too small, squat bending may become difficult. For optimal performance, θ should be set somewhere between 20 degrees and 45 degrees while the wearer is in the standing position. When in a standing position, this harness restricts the wearer from forward bending past angle $\theta_1$, as illustrated in FIG. 4. As the wearer begins to bend their knees, however, angle θ begins to increase, allowing just enough slack for the wearer to perform the squat bending movement with no resistance from the harness. In FIG. 5, the maximum allowable forward bending angle has increased to $\theta_2$ and is labeled along with an additional angle α, which can be defined as the angle between lines parallel to the wearers upper leg (thigh) and lower leg. Once angle θ is set, as described above, any further increase in θ can be directly related to a decrease in α. The rate at which θ increases in relation to the decrease in a ($\Delta\theta/\Delta\alpha$) can be adjusted for optimal performance, and this is the final adjustment the wearer must make. In order to adjust this rate ($\Delta\theta/\Delta\alpha$), the wearer must reposition slide adjusters 60 and 44. For optimal performance, these slide adjusters should always be equally spaced above each foot, and any repositioning should be done equally for both. Raising both slide adjusters 60 and 44 will reduce the amount θ increases in relation to a decreasing α. Lowering both slide adjusters 60 and 44 will increase the rate at which θ increases in relation to a decreasing α. For example, if slide adjusters 60 and 44 are raised too high, angle θ will not increase at a sufficient rate to allow enough slack for the wearer to perform the squat bending movement. If slide adjusters 60 and 44 are positioned too low, there will be excess slack, and the wearer would potentially be able to forward bend completely after only slightly bending the knees. To properly adjust this rate, the wearer should begin with both slide adjusters 60 and 44 positioned approximately 8 cm (around 3 inches) above each foot. The wearer should then squat and determine by the amount of slack available if these slide adjusters should be raised or lowered. For optimal performance, there should be just enough slack available as the wearer bends their knees to allow comfortable squat bending, and no more. As the wearer walks, lower right strap 38 will be pulled back and forth through D-ring 34 as the wearer's legs move. This slippage through D-ring 34 provides the necessary slack to allow the wearer to walk normally without their legs being uncomfortably restricted by the harness. For optimal performance, the coefficient of friction between D-ring 34 and lower right strap 38 should be as low as possible, and as stated above, most common nylon straps and plastic D-rings would be suitable. If the wearer prefers to have lower left leg strap 56 and lower right leg strap 38 more securely attached to their legs, they can employ the use of the optional components illustrated in FIG. 6. The optional right leg strap 66 and optional left leg strap 68 will secure lower left strap 56 and lower right strap 38 in place. The optional right leg strap 66 and optional left leg strap 68 should be wrapped around their respective legs, and their ends should be fastened in some manner such as with the hook and loop fastener 70 illustrated in FIG. 6. These optional leg straps are not required for this harness to function properly, however, if left foot hole 64 or right foot hole 48 become loose or seem to be sliding forward, these optional straps would be helpful. The straps 66 and 68 should be attached to the straps 56 and 38 just above the foot holes 48 and 64 preferably by attaching the straps 66 and 68 to the straps 56 and 38 between the upper and lower slide adjusters 44, 46 and 60, 62.

Accordingly, the reader will see that this forward bending motion control harness provides a new and practical way to protect the injury prone lower back. While this device prevents the dangerous forward bending motion, it also allows the wearer to perform tasks that require bending by allowing the wearer to bend using the squatting method (i.e. squatting with straight back and bent knees), a feature not found in any prior art. This harness is also small, lightweight, durable, low cost, and easily adjusts to fit nearly any body type. Additionally, because these harnesses could be relatively simple to manufacture and are made from common components, they should in turn be easily affordable to any organization wishing to implement their use. And although this harness would most likely be used primarily in industry, it also would be a valuable safety device for other activities, such as weight lifting, gardening, or any other activity that requires bending and lifting.

While my above description contains many specifities, these should not be construed as limitations on the scope of the invention, but rather as an exemplification of one preferred embodiment thereof. Many variations are possible. For example, the straps used for this harness could be replaced with a similar material, such as cable. If cable was used to replace the lower right and lower left straps, a pulley could be used in place of the D-ring to allow the necessary slippage for unrestricted walking. The slide adjusters and strap locking buckles could potentially be replaced with other types of similar hardware. The strap composing the left and right foot holes could be reinforced or replaced with a more durable material to help prevent wear. Instead of having left and right foot holes, these straps could be attached to the wearer's shoes using any variety of clips or fasteners to avoid having the straps go under the wearer's feet. Accordingly, the scope of the invention should not be determined by the embodiment illustrated, but by the appended claims and their legal equivalents.

I claim:

1. A harness for restricting back angles of a user when lifting comprising:

a back strap having a top end and a bottom end, for alignment with the spinal column of a user's back, a left shoulder strap having a first end attached at the top of the back strap and a second end having a strap locking buckle attached thereto, a right shoulder strap having a first end attached at the top of the back strap and a second end having a strap locking buckle attached thereto, a left connector strap having a first end attached to the back strap below the attachment point of the left shoulder strap, and a second end for adjustably connecting the left connector strap to the strap locking buckle on the left shoulder strap, a right connector strap having a first end attached to the back strap below the attachment point of the right shoulder strap, and a second end for adjustably connecting the right connector strap to the strap locking buckle on the right shoulder strap, a ring attached at the bottom of the back strap, a lower right strap passing through the ring, the lower right strap having a first end and a second end, the first end having an adjustable strap locking buckle slidably attached thereto, the second end passing through an upper right slide adjuster and a lower right slide adjuster forming a foot loop and then returning through the lower right slide adjuster and the upper right slide adjuster and having the second end fixedly attached to the lower right strap, such that a leg loop is formed between the second end and the upper slide adjuster, a lower left strap, the lower left strap having a first end and a second end, the second end passing through an upper left slide adjuster and a lower left slide adjuster forming a foot loop and then returning through the lower left slide adjuster and the upper left slide adjuster and having a second end fixedly attached to the lower left strap, such that a leg loop is formed between the second end and the upper slide adjuster, the first end connected to the adjustable strap locking buckle on the lower right strap, such that the user can bend to a first angle when standing and to a second angle when squatting and adjust said first and second angles by moving the lower right strap relative to the strap locking buckle to adjust the first angle and the upper slide adjuster of the lower left strap and the lower right strap for adjusting the second angle.

2. A harness for restricting back angles when lifting as in claim 1 wherein, the ring is a D-ring attached to the bottom of the back strap by folding the back strap over forming a loop of material encasing the D-ring and stitching the back strap to itself.

3. A harness for restricting back angles when lifting as in claim 1 wherein, a pad attached to the bottom of the back strap protects the user's back from pressure from the ring.

4. A harness for restricting back angles when lifting as in claim 1 wherein, a right leg strap passing around the right leg of the wearer and the portion of the lower right strap between the upper right slide adjuster and lower right slide adjuster for securing the lower portion of the lower right strap to the right leg of the wearer, and a left leg strap passing around the left leg of the wearer and the portion of the lower left strap between the upper left slide adjuster and lower left slide adjuster for securing the lower portion of the lower left strap to the left leg of the wearer.

5. A harness for restricting back angles of a user when lifting comprising:

a back strap having a top end and a bottom end for alignment with the spinal column of a user's back, a left shoulder strap connected to the back strap to secure the upper portion of the back strap to the user, a right shoulder strap connected to the back strap to secure the upper portion of the back strap to the user, a ring attached at the bottom of the back strap, a lower right strap passing through the ring, the lower right strap having a first end and a second end, the first end having an adjustable strap locking buckle, the second end passing through an upper right slide adjuster and a lower right slide adjuster forming a loop and then returning through the lower right slide adjuster and the upper right slide adjuster and having the second end fixedly attached to the lower right strap, such that a leg loop is formed between the second end and the upper slide adjuster, a lower left strap, the lower left strap having a first end and a second end, the second end passing through an upper left slide adjuster and a lower left slide adjuster forming a loop and then returning through the lower left slide adjuster and the upper left slide adjuster and having a second end fixedly attached to the lower left strap, such that a leg loop is formed between the second end and the upper slide adjuster, the first end connected to the adjustable strap locking buckle on the lower right strap, such that the lower right strap can slide on the ring when user is walking, such that the user can bend to a first angle when standing and to a second angle when squatting.

6. A harness for restricting back angles when lifting as in claim 5 wherein, the ring is a D-ring attached to the bottom of the back strap by folding the back strap over forming a loop of material encasing the D-ring and stitching the back strap to itself.

7. A harness for restricting back angles when lifting as in claim 5 wherein, a pad attached to the bottom of the back strap protects the user's back from pressure from the ring.

8. A harness for restricting back angles when lifting as in claim 5 wherein, a right leg strap passing around the right leg of the wearer and the portion of the lower right strap between the upper right slide adjuster and lower right slide adjuster for securing the lower portion of the lower right strap to the right leg of the wearer, and a left leg strap passing around the left leg of the wearer and the portion of the lower left strap between the upper left slide adjuster and lower left slide adjuster for securing the lower portion of the lower left strap to the left leg of the wearer.

9. A harness for restricting back angles of a user when lifting comprising:

a back strap having a top end and a bottom end for alignment with the spinal column of a user's back, a means for attaching the shoulders of the user to the top end of the back strap, a ring attached at the bottom of the back strap, an adjustable length strap passing through the ring and having a first end attachable to a first foot of a user and a second end attached to a second foot of a user, such that the user can bend to a first angle when standing and to a second angle when squatting.

10. A harness for restricting back angles when lifting as in claim 9 wherein, the ring is a D-ring attached to the bottom of the back strap by folding the back strap over forming a loop of material encasing the D-ring and stitching the back strap to itself.

11. A harness for restricting back angles when lifting as in claim 9 wherein, a pad attached to the bottom of the back strap protects the user's back from pressure from the ring.

12. A harness for restricting back angles when lifting as in claim 9 wherein, a right leg strap attached to the adjustable strap near the first end, for securing the first end to the user's right leg, a left leg strap attached to the adjustable strap near the second end, for securing the second end to the user's left leg.

* * * * *